(12) United States Patent
Liu et al.

(10) Patent No.: US 7,587,951 B2
(45) Date of Patent: Sep. 15, 2009

(54) THERMOPHORESIS-RESISTANT GAS DILUTION APPARATUS FOR USE IN EMISSIONS ANALYSIS

(75) Inventors: Zhili Gerald Liu, Madison, WI (US); Thaddeus Alan Swor, St. Paul, MN (US); James Alan Debilzen, Brooklyn, WI (US); Casey Lee Severance, Madison, WI (US)

(73) Assignee: Cummins Filtration IP Inc., Minneapolis, MN (US)

( * ) Notice: Subject to any disclaimer, the term of this patent is extended or adjusted under 35 U.S.C. 154(b) by 345 days.

(21) Appl. No.: 11/530,758

(22) Filed: Sep. 11, 2006

(65) Prior Publication Data

US 2008/0060453 A1    Mar. 13, 2008

(51) Int. Cl.
*G01N 1/38* (2006.01)
(52) U.S. Cl. .............. 73/863.51; 73/863.11; 73/23.31; 436/179
(58) Field of Classification Search ............. 73/23.31, 73/863.11, 863.12, 863.51; 436/179
See application file for complete search history.

(56) References Cited

U.S. PATENT DOCUMENTS

| | | | | |
|---|---|---|---|---|
| 5,058,440 A | * | 10/1991 | Graze, Jr. ............... | 73/863.83 |
| 7,021,130 B2 | | 4/2006 | Schmidt | |
| 7,328,629 B2 | * | 2/2008 | Farthing et al. ......... | 73/863.11 |
| 7,363,828 B2 | * | 4/2008 | Liu ........................ | 73/863.03 |
| 7,418,881 B2 | * | 9/2008 | Watson et al. ........... | 73/865.5 |
| 2006/0130599 A1 | * | 6/2006 | Graze, Jr. ............... | 73/864.73 |

OTHER PUBLICATIONS

U.S. Appl. No. 11/530,728, filed Sep. 2006, Liu et al.
U.S. Appl. No. 11/530,746, filed Sep. 2006, Liu et al.
http://www.sciencedaily.com/release/2006/06/060625124445.htm.
Hildeman et al., "Chemical Composition of Emissions from Urban Sources of Fine Organic Aerosol.", Environ. Sci. Technol., vol. 25, No. 4, 1991, pp. 744-759.
Hildeman et al., "A Dilution Stack Sampler For Collection of Organic Aerosol Emissions: Design, Characterization and Field Tests", Aerosol Science and Technology, vol. 10, 1989, pp.193-204.

(Continued)

*Primary Examiner*—Hezron Williams
*Assistant Examiner*—Nashmiya S Fayyaz
(74) *Attorney, Agent, or Firm*—Hamre, Schumann, Mueller & Larson, P.C.; J. Bruce Schelkopf (57) ABSTRACT

A thermophoresis-resistant dilution apparatus for dilution of gas from an emission source, such as a combustion engine, for example a gasoline, diesel or natural gas engine. The apparatus is designed to simulate atmospheric dilution, mixing and cooling processes, enabling sampled emission gas and dilution air to thoroughly mix and cool to ambient temperature, allowing some volatile and semi-volatile gas-phase organics to nucleate, condense and coagulate to their usual aerosol phase. The apparatus is designed to resist thermophorectic forces acting on the particulate matter in the sampled emission gas, thereby preventing particulate matter losses. In addition, the apparatus evenly distributes the dilution air into the sampled gas for improved mixing.

24 Claims, 9 Drawing Sheets

OTHER PUBLICATIONS

Kleeman et al., "Size and Composition Distribution of Fine Particulate Matter Emitted from Motor Vehicles", Environmental Science & Technology, vol. 34, No. 7, 2000, pp. 1132-1142.

Kweon et al., "Detailed Chemical Composition and Particle Size Assessment of Diesel Engine Exhaust," SAE 2002-01-2670, Fall SAE Meeting 2002, pp. 1-13.

Liu et al., "Transient Performance of Diesel Particulate Filters as Measured by an Engine Exhaust Particle Size Spectrometer", 2005-01-0185, 2005 SAE International, pp. 1-10.

Liu et al., "Transient Analysis of Engine Nano-Particles Using a Fast-Scanning Differential Mobility Particle Analyzer", 2004-01-0971, 2004 SAE International, pp. 1-14.

Liu et al., "Diesel Particulate Filters: Trends and Implications of Particle Size Distribution Measurement", 2003-01-0046, 2003 Society of Automotive Engineers, Inc., pp. 1-14.

MacGibbon et al., "The Effect of Thermophoresis on Particle Deposition in a Tungsten Low Pressure Chemical Vapor Deposition Reactor", Journal of The Electrochemical Society, vol. 146, No. 8, 1999, pp. 2901-2905.

Schauer et al., "Measurement of Emissions from Air Pollution Sources. 2. $C_1$ through $C_{30}$ Organic Compounds from Medium Duty Diesel Trucks", Environmental Science & Technology, vol. 33, No. 10, 1999, pp. 1578-1587.

\* cited by examiner

Fig. 9

THERMOPHORESIS-RESISTANT GAS DILUTION APPARATUS FOR USE IN EMISSIONS ANALYSIS

FIELD

An apparatus for diluting a gas that is to be analyzed. In particular, a thermophoresis-resistant dilution apparatus for dilution of gas from an emission source, such as an internal combustion engine, for example a gasoline, diesel or natural gas engine.

BACKGROUND

Emissions of pollutant chemicals have increased orders of magnitudes in the past 100 years due primarily to anthropogenic releases associated with industrial, agricultural, domestic, and recreational activity. Current research indicates that there are very strong correlations between the increase in these emissions and an overall increase in atmospheric temperatures (Global Warming) and an increased number of Category 4 and 5 hurricanes per annum. Furthermore, it is believed that ambient particulate matter in aerosol phase may include potentially toxic components. Researchers believe that particulate matter and gases may cause various health problems, such as asthma. The correlations between emissions of pollutant chemicals and the negative impact on environment and human health has led to more stringent worldwide emission standards.

In order to meet the emission standards of today and the future, researchers have made, and are continually striving to make, improvements to combustion engines, for example heavy duty diesel engines, gas combustion engines, power-generating gas turbines, and the like, and other emission sources. In addition to these developments, researchers are endeavoring for better methods and devices of measuring smaller particulate matter and quantifying the chemical compositions of trace emissions.

Generally, chemical composition analysis of fine particulate matter, inorganic gases, and volatile and semi-volatile organic compounds from emissions sources comprises three major steps: (1) Representative conditioning and sampling; (2) Chemical analysis; and (3) Data analysis and explanation. The effective accuracies of Steps (2) and (3) are both dependent on step (1). For without an accurate and precise sampling procedure, no analysis of that sample could be said to represent valid data. Accordingly, without valid analysis, full and complete explanation of the sample would not be available.

In collecting emission source samples, it is known to introduce a dilution gas, usually conditioned air (particulate matter, humidity, temperature, and gases controlled air), into the emission gas in order to dilute and cool the emission gas to near ambient conditions. This is intended to permit the sample gases to nucleate, condense and coagulate, and to be aged in a residence time chamber to their usual phases and conditions as if they were emitted to the atmosphere. For example, see L. M. Hildeman, G. R. Cass, and G. R. Markowski, "A Dilution Stack Sampler For Collection of Organic Aerosol Emissions: Design, Characterization and Field Tests", Aerosol Science and Technology, Vol. 10, pp. 193-204, 1989.

Figure 1:
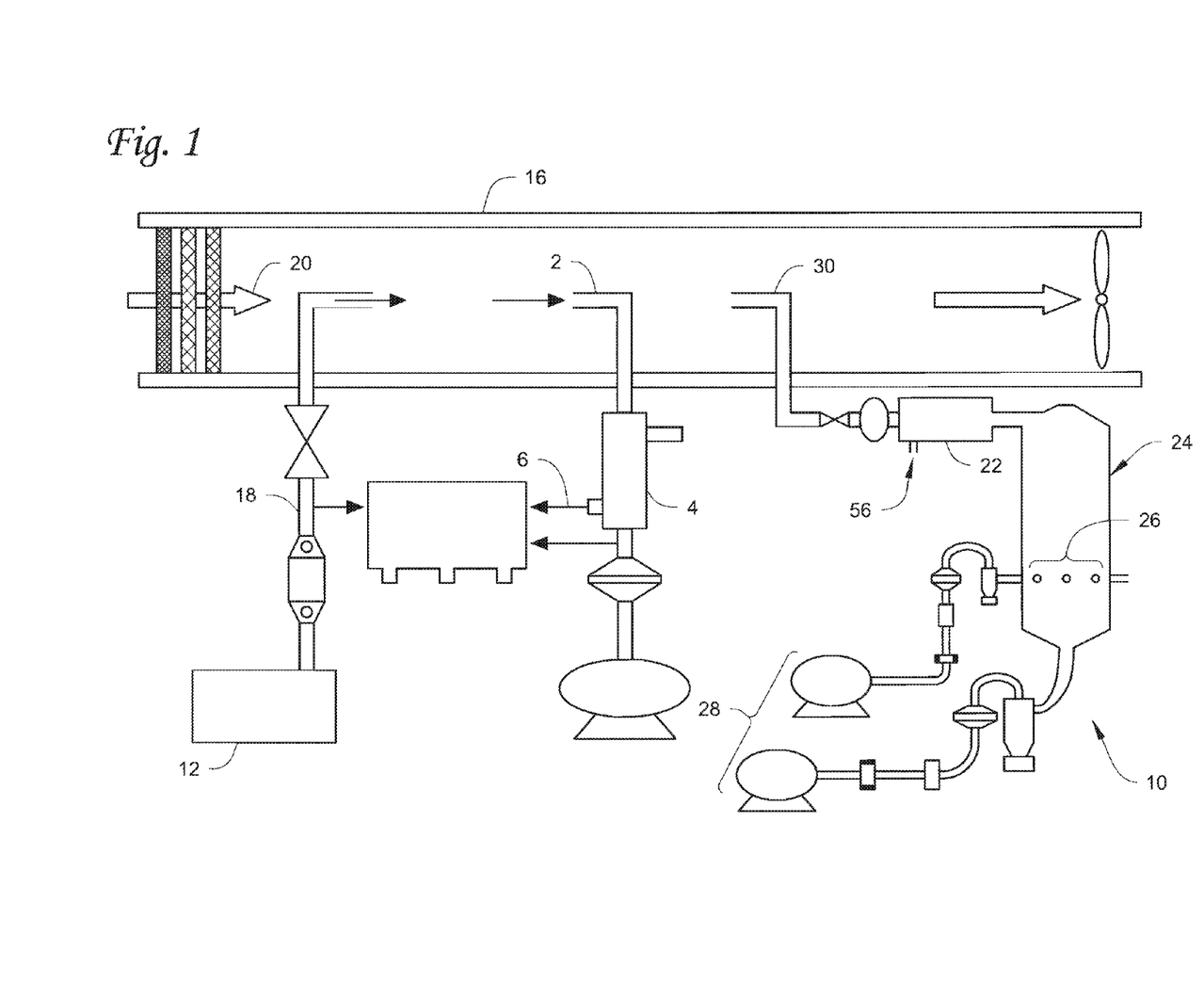
FIG. 1 illustrates an example of a sampling system in which the dilution apparatus can be used.

In the United States, the typical system for assessing particulate matter mass emissions mixes emission gas with filtered air in a mixing chamber. The typical system is illustrated in FIG. 1, and includes a sampling port 2 that feeds exhaust gases to a diluter 4, forming the mixing chamber, where the exhaust gases are diluted with the filtered air. The diluted gas mixture is then sampled by a sampling train 6 to collect particulate matter mass. However, this typical system doesn't minimize a temperature gradient between sample gases and the inner wall of the mixing chamber and therefore may cause significant loss of sample particles during the dilution processes.

Work at the University of Wisconsin-Madison attempted to improve the traditional system. The University of Wisconsin scientists used a device called an "augmented sampling system" to study the chemical composition and to assess particle size of diesel engine exhaust. (Chol-Bum Kweon, David E. Foster, James J. Schauer, and Shusuke Okada, "Detailed Chemical Composition and Particle Size Assessment of Diesel Engine Exhaust" SAE 2002-01-2670, Fall SAE Meeting 2002) The "augmented sampling system" disclosed by Kweon et al includes a secondary dilution tunnel for the diesel exhaust and a residence time chamber with radial sampling ports near the base of the residence time chamber. The secondary dilution tunnel of the augmented sampling system mixes filtered air with an emission gas sample without regard to temperature gradient between the surface of the dilution tunnel and the emission gas. This may lead to a high degree of particle loss and accordingly less accurate sampling due to thermophoresis.

Thermophoresis, or Ludwig-Soret effect, is thought to be related to Brownian movement biased by a temperature gradient. The thermophoretic force is a force that arises from asymmetrical interactions of a particle with the surrounding gas molecules due to a temperature gradient. Generally, a particle is repelled from a hotter surface and attracted to a cooler surface. Thus, as emission particles travel through a sampling system, cooler surface temperature of the system as compared to the emission gas would lead to greater attraction on the emission particles.

In the Kweon et al. augmented sampling system, the residence time chamber is heated to reduce thermophoresis. However, the heated residence time chamber is likely to fail in simulating realistic atmospheric conditions, as the addition of heat may affect the aging, nucleation, condensation, and coagulation processes of particulate matter, volatile organic compounds and semi-volatile organic compounds and the secondary reaction of inorganic and organic compounds.

An apparatus that allows for mixing of sampled emission gas with conditioned air to dilute the emission sample and reduce particle loss due to thermophoresis is needed. An improvement in the diluting process is desirable because it may lead to a more accurate and precise sampling from the sample source and thus contribute to more accurate results.

SUMMARY

An apparatus that resolves these and other problems of conventional emissions source diluters is provided. In particular, a thermophoresis-resistant dilution apparatus is provided for dilution of gas from an emission source, such as a combustion engine, for example a gasoline, diesel or natural gas engine.

The apparatus is designed to simulate atmospheric dilution, mixing and cooling processes, enabling sampled emission gas and dilution air to thoroughly mix and cool to ambient temperature, allowing volatile and some semi-volatile gas-phase organics to nucleate, condense and coagulate to their usual aerosol phase. The apparatus is designed to resist thermophoretic forces acting on the particulate matter in the sampled emission gas, thereby preventing particulate matter losses. In addition, the apparatus evenly distributes the dilution gas into the sampled gas for improved mixing.

In one version, a thermophoresis-resistant gas dilution apparatus includes a housing having a first end and a second end and defining an interior space, with the second end including an exit port in communication with the interior space through which gas exits the apparatus. A wall is disposed within the interior space of the housing and divides the interior space into an inner flow path defined by the wall and an outer flow path defined between the housing and the wall, with the inner flow path being in communication with the exit port. A gas stream inlet is provided adjacent the first end of the housing that opens into the inner flow path to permit introduction of a gas stream into the inner flow path. In addition, a dilution gas inlet is provided in the housing adjacent to the second end thereof, with the dilution gas inlet opening into the outer flow path to permit introduction of dilution gas into the outer flow path. In addition, a plurality of holes in the wall that are axially spaced from the dilution gas inlet place the outer flow path in communication with the inner flow path.

In this construction, the dilution gas in the outer flow path flows in a direction opposite to the gas stream in the inner flow path toward the holes. During this time, the dilution gas exchanges heat with the gas stream, thereby lowering the temperature of the gas stream and increasing the temperature of the dilution gas. The dilution gas is then introduced into the gas stream through the holes which additionally cools the gas stream and the gas stream and dilution gas can thoroughly mix.

In another version, a gas stream dilution apparatus for a source dilution sampling system includes a cylindrical housing having a first end, a second end and an interior space. An inner cylindrical wall is located concentrically with the housing, with the cylindrical wall having a first end adjacent the first end of the housing and a second end adjacent the second end of the housing. The cylindrical wall divides the interior space into a static pressure chamber defined between the housing and the wall and that extends generally from the first end of the wall to the second end of the wall, and a mixing chamber that extends generally from the first end of the wall to the second end of the wall. The wall has circumferentially and axially distributed perforations near the first end thereof that place the static pressure chamber in communication with the mixing chamber. In addition, the housing has a plurality of inlet ports near the second end thereof that open into the static pressure chamber for introducing a dilution gas into the static pressure chamber. An inlet port that is adjacent the first end of the housing opens into the mixing chamber for introducing a gas stream into the mixing chamber, and the perforations in the wall allow for the distribution into and mixing of dilution gas with a gas stream in the mixing chamber.

In another version, the dilution air is heated (or cooled) and the mixture of sample gas and dilution air can reach the upper limit of the desired temperature, for example within 5° C. of the desired temperature, more preferably reach ambient temperature.

In another version, the flow rate of the dilution air is controlled through valves or over-pressure of the dilution air (created by a compressor) to achieve the desired dilution ratio. Dilution ratio is defined as the ratio of the total flow rate of the gas mixture (i.e. sample gas and dilution air) to that of the raw sample gas.

In yet another version, a coated thin insulation material or a sealed chamber filled with insulation is attached to the inner wall. The insulation extends from generally the second end of the wall to generally the perforation pattern. The insulation is meant to reduce heat transfer from the sample gas to the dilution gas, lowering the effect of thermophoresis by keeping the inner part of the wall the same temperature as the sample gas flowing through it.

A method of simulating atmospheric dilution, mixing and cooling of a gas stream is also provided. The method includes introducing a gas stream at a first temperature into a first chamber in which the gas stream can flow from a first end to a second end, and introducing a dilution gas at a second temperature lower than the first temperature into a second chamber surrounding the first chamber and in heat exchanging relationship therewith so that the dilution gas in the second chamber exchanges heat with the gas stream in the first chamber, and with the dilution gas flowing through the second chamber in a direction opposite the direction of flow of the gas stream. After a period of heat exchange between the dilution gas and the gas stream, the dilution gas is evenly introduced into the gas stream in the first chamber between the first end and the second end.

DETAILED DESCRIPTION

With reference to FIG. 1, a system 10 for sampling emissions products from an emissions source 12 is illustrated. As illustrated, the system 10 is constructed to simultaneously sample a number of different emissions products emitted from the emissions source 12. The samples can then be analyzed to permit chemical characterization of the emissions products with respect to air toxics.

The system 10 can be used to great advantage in sampling a number of types of gases from a number of other types of emissions sources, both stationary and mobile sources. Examples of gases that can be sampled includes, but is not limited to, diesel engine exhaust, gasoline engine exhaust, natural gas engine exhaust, turbine engine exhaust, and atmospheric gas. Examples of emissions sources includes, but is not limited to, diesel engines, gasoline engines, natural gas engines, turbine engines, power plants, manufacturing plants, exhaust stacks, etc. To facilitate the description, the emissions source 12 will be described herein as being a diesel engine and the gas to be sampled as exhaust from the diesel engine.

As shown in FIG. 1, the exhaust from the engine 12 is ducted to a dilution tunnel 16 through suitable piping 18. Filtered dilution air 20 is introduced into the tunnel upstream of the discharge for the engine exhaust, with the dilution air 20 then mixing with the engine exhaust in the tunnel 16 to dilute and cool the exhaust gas.

The system 10 includes a dilution apparatus 22, a residence time chamber 24, a plurality of sampling probes 26 within the residence time chamber, and a plurality of sampling trains 28 connected to the sampling probes to take simultaneous representative emission samples for subsequent analysis.

The dilution apparatus 22 is connected to a sampling probe 30 that extends into the dilution tunnel 16. The probe 30 collects a gas stream sample from the engine 12 and directs the gas stream sample to the dilution apparatus 22. In the dilution apparatus 22, the sampled gas is diluted with dilution gas, cooled (for example to ambient temperature), and thoroughly mixed with the dilution gas.

The gas mixture is then fed to the residence time chamber 24 which is designed to provide sufficient time for sample aging and gas-to-particle conversion, which involves the diffusion limited transport of supersaturated vapor onto existing particles. The gas flow also becomes uniformly distributed before entering the sampling the sampling probes 26. The sampling probes 26 simultaneously collect multiple samples of the gas mixture and feed the samples to the sampling trains 28 which are constructed to take various samples of the gas, for example to sample volatile and semi-volatile organics, gas-phase inorganics, and particulate matter.

Further details on the system 10 and its operation can be found in copending U.S. patent application Ser. No. 11/530728, filed on Sept. 11, 2006, and titled Source Dilution Sampling System For Emissions Analysis, which application is incorporated herein by reference.

With reference to FIGS. 2-6, the dilution apparatus 22 is designed to be thermophoresis-resistant to reduce the thermophoretic force on emission particles in the sampled gas, thereby reducing particulate matter losses. In addition, the dilution apparatus 22 preferably simulates atmospheric dilution, mixing and cooling processes, enabling the sampled gas and the dilution gas to thoroughly mix and cool to ambient temperature, allowing sample gas to age and some volatile and semi-volatile gas-phase organics in the sampled gas to nucleate, condense and coagulate to their usual aerosol phase.

The sampled gas collected by the sampling probe 30 enters the dilution apparatus 22 through an inlet 32. As shown in FIGS. 2-6, the dilution apparatus 22 has a cylindrical housing 34 with a first end 36 that includes the inlet 32, a second end 38 and an interior space. An inner cylindrical wall 40 is located concentrically with the housing 34, with the cylindrical wall 40 having a first end 42 adjacent the first end 36 of the housing and a second end 44 adjacent the second end 38 of the housing. The cylindrical wall 40 divides the interior space into a static pressure chamber 46 defined between the housing 34 and the wall 40 and that extends generally from the first end 42 of the wall to the second end 44 of the wall 40, and a mixing chamber 48 that extends generally from the first end of the wall to the second end of the wall.

Figure 3:
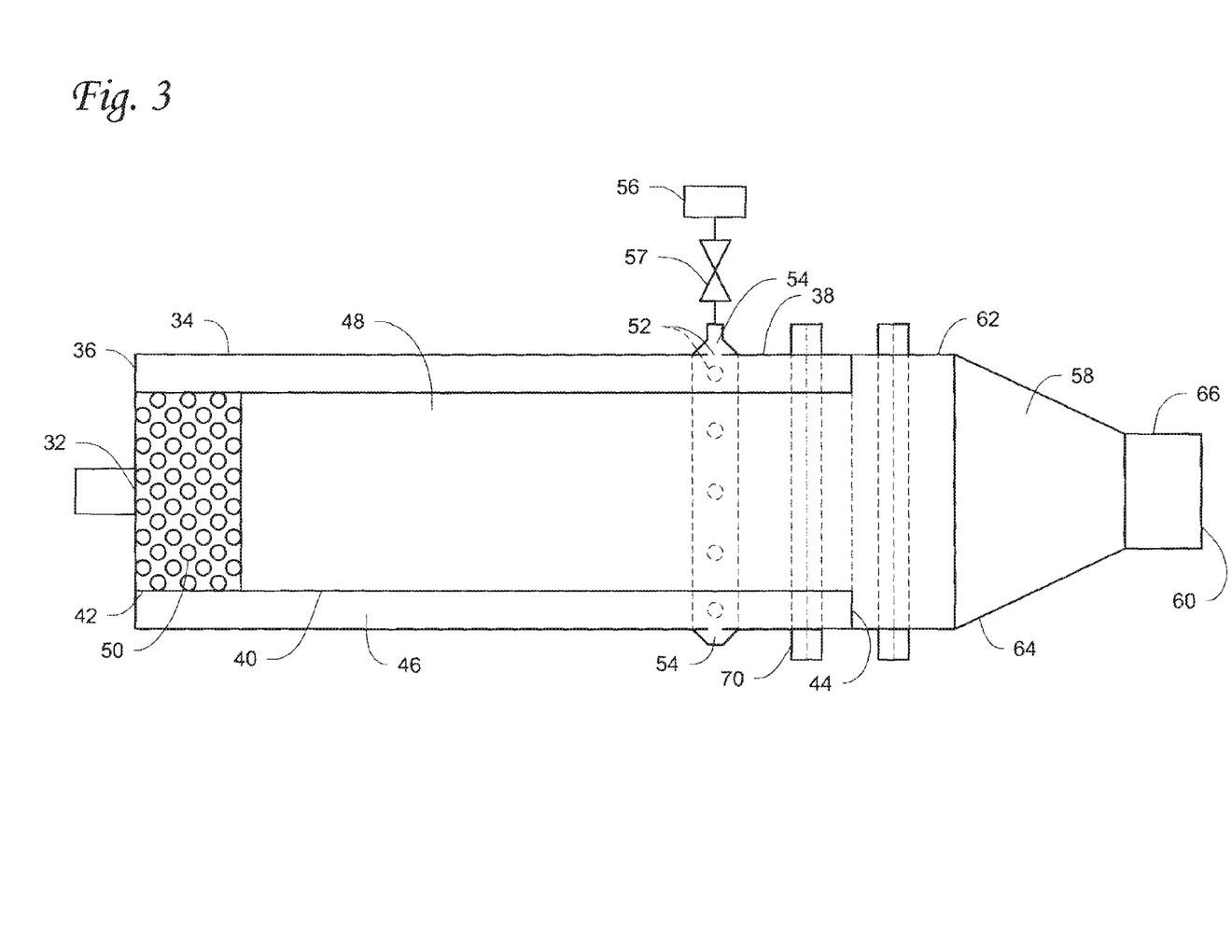
FIG. 3 is a cross-sectional view of the dilution apparatus taken along the longitudinal axis thereof.

The wall 40 has circumferentially and axially distributed perforations 50 near the first end 42 thereof that place the static pressure chamber 46 in communication with the mixing chamber 48. In addition, the housing 34 has a plurality of evenly, circumferentially spaced inlet ports 52 near the second end 44 thereof that open radially into the static pressure chamber 46 for introducing a dilution gas into the static pressure chamber 46. As shown in FIG. 3, the inlets ports 52 communicate with a plenum 54 defined around the circumference of the housing 34, and dilution gas is fed to the plenum 54 from a dilution gas source 56.

Figure 9:
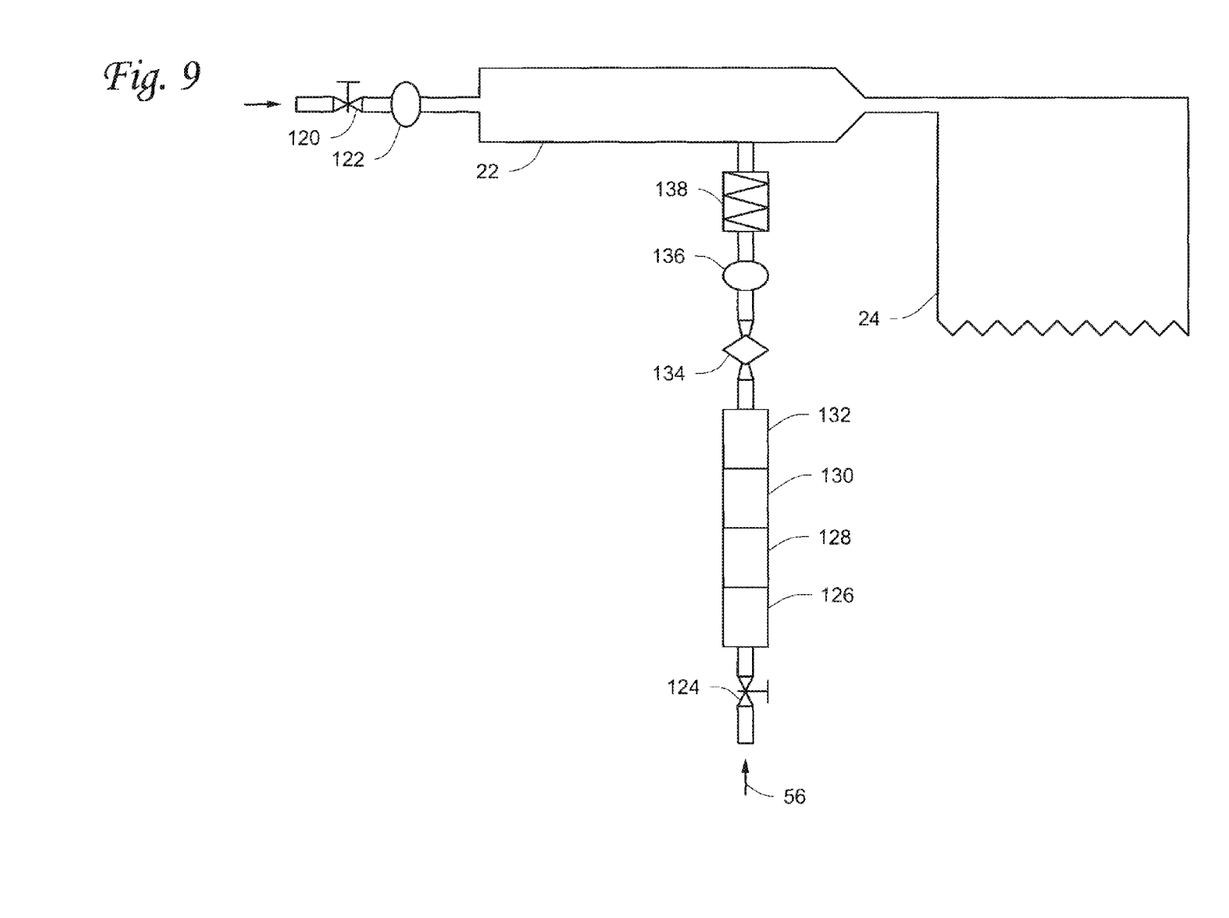
FIG. 9 is a view of the dilution apparatus illustrating how to regulate dilution ratio, how to condition the dilution air, and how to heat or cool the dilution air.

As illustrated in FIG. 9, means can be provided to control dilution ratio, means can be provided to condition the dilution gas, and means can be provided to heat or cool the dilution gas. For example, as shown in FIG. 9, the dilution gas source 56 can be a source of over-pressure, such as a compressor. A valve 120 is provided upstream of the apparatus 22, with inlet flow of sampled gas being monitored by a flow meter 122. A valve 124 controls the flow of dilution gas from the gas source 56. The dilution gas then flows through a series of gas conditioners, for example a pre-filter 126, a moisture filter 128, a volatile absorption substrate 130, and a high efficiency particle arrester (HEPA) filter 132. A pressure regulator 134, such as a valve, regulates the flow of dilution gas from the gas conditioners and into the apparatus 22, monitored by a flow meter 136. A heat exchanger 138 can also be provided to heat or cool the dilution gas.

The dilution ratio, which is defined as the ratio of the total flow rate of the gas mixture (i.e. sample gas and dilution gas) to that of the raw sample gas, is controlled by the valves 120, 124 and pressure regulator 134, with monitoring of the flow of the sampled gas and dilution gas monitored by the flow meters 122, 136. The dilution gas is conditioned by one or more of the pre-filter 126, the moisture filter 128, the volatile absorption substrate 130, and the HEPA filter 132. In addition, heating or cooling of the dilution gas is achieved through suitable heating or cooling by the heat exchanger 138.

Figure 4:
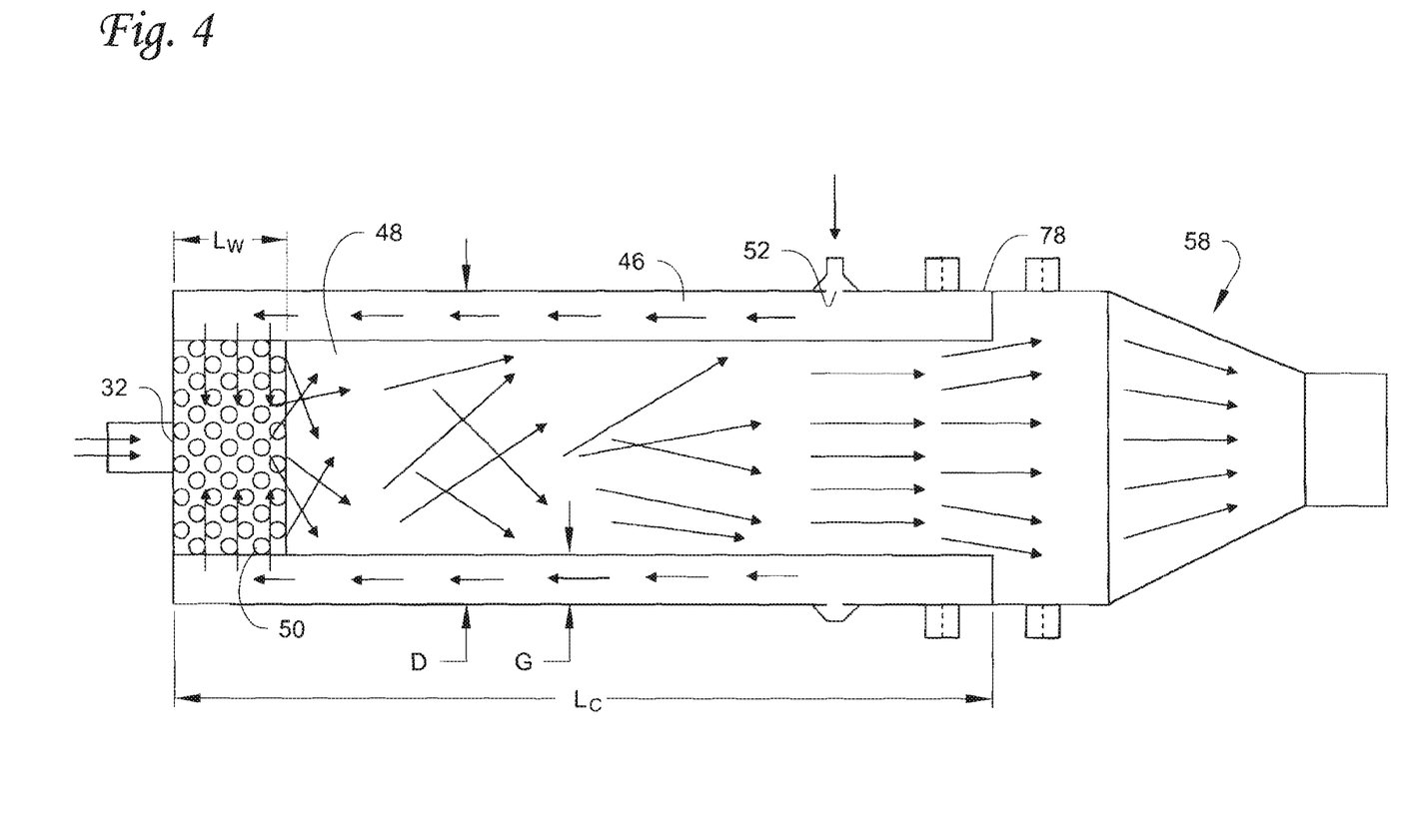
FIG. 4 is a view similar to FIG. 3 with arrows indicating the flow of sampled gas and dilution gas within the dilution apparatus.

In use, the sampled gas enters the mixing chamber 48 of the dilution apparatus through the inlet 32 as shown by the arrows in FIG. 4. In addition, dilution gas is introduced into the static pressure chamber 46 through the inlets ports 52. As the dilution gas flows toward the first end 42 as shown by the arrows in FIG. 4, it exchanges heat with the sampled gas in the mixing chamber 48.

Figure 5:
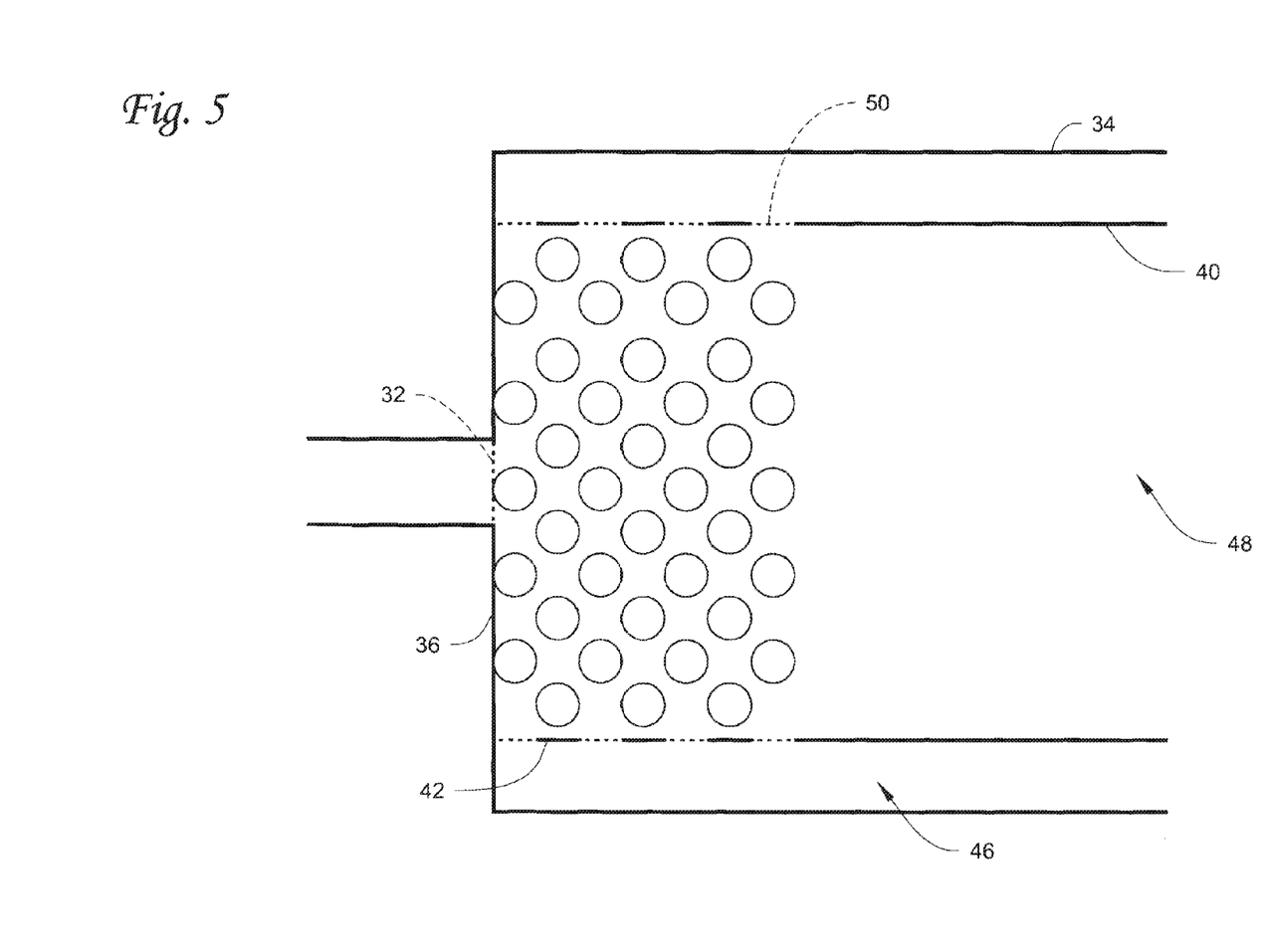
FIG. 5 is a partial sectional view of the dilution apparatus showing the sampled gas inlet and the perforation pattern of the inner tube.

Once the dilution gas reaches the perforations 50, it flows radially inward into the mixing chamber 48 to mix with the sampled gas. FIG. 4 illustrates the flow of dilution air into the mixing chamber 48. The perforation holes 50 create jets of dilution air that impinge upon the sampled gas to create turbulent mixing with the sampled gas. Preferably, the perforation holes 50 are configured to generally evenly distribute the dilution gas into the mixing chamber. As shown in FIG. 5, the holes 50 are circumferentially and axially evenly spaced about the wall 40. Mixing of the dilution gas and the sampled gas also cools the sampled gas.

The dilution gas is at a temperature lower than the sampled gas, so that the sampled gas is cooled through heat exchange with the static pressure chamber and as a result of mixing with the dilution gas. Preferably, the sampled gas is cooled to ambient temperature, allowing some volatile and semi-volatile gas-phase organics in the sampled gas to nucleate, condense and coagulate to their usual aerosol phase in the atmosphere.

In addition, because the sampled gas is cooled while exchanging heat with the dilution gas that flows in the opposite direction, temperature differences between the static pressure chamber 46 and the mixing chamber 48 is smaller than the temperature difference between that of the exterior of the apparatus 22 and the mixing chamber 48, thereby reducing the thermophoretic force acting on particles in the flow. This reduces particle loss as the gas sample flows through the dilution apparatus 22.

The number and size of the perforation holes 50 is chosen based on the gas being sampled and the desired dilution rate. For diesel engine exhaust, the holes can provide between 20% to 80% porosity, have diameters ranging from about 0.125 inch to about 0.5 inch, and extend over a length $L_w$ of the wall 40 ranging from about 0.06 inches to about 15 inches (FIG. 4). In addition, the dimensions of the dilution apparatus 22 are chosen based on the temperature of the sampled gas and the flow rate. With reference to FIG. 4, for diesel engine exhaust, the length $L_c$ of the mixing chamber 48 can vary between 18.0 inches to 63.0 inches, the housing can have a diameter D between 3.0 inches and 10.5 inches, and the gap G defining the static pressure chamber between the wall 40 and the housing 34 can vary between 0.2 inches and 2.0 inches.

Figure 7:
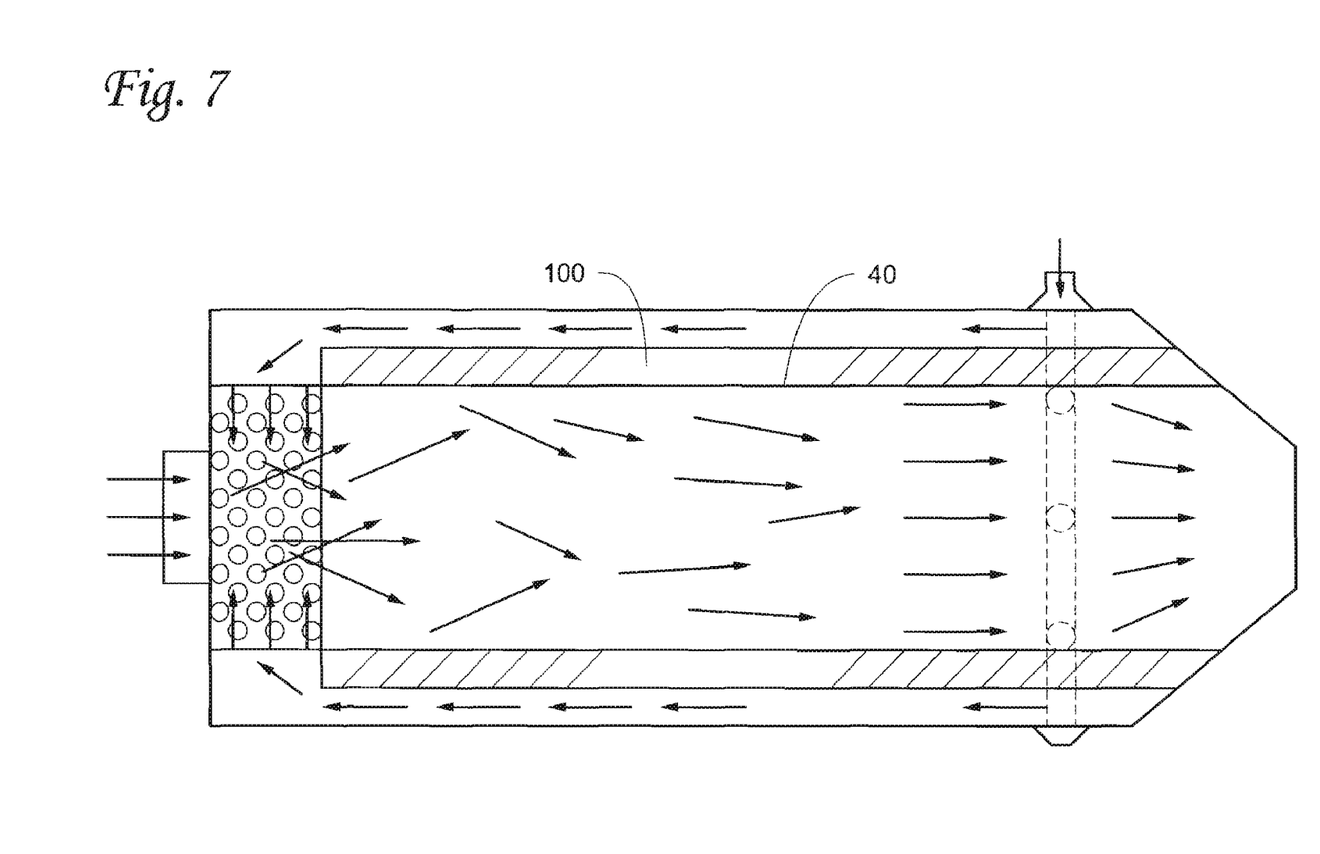
FIG. 7 is a view of an embodiment with an insulation layer on the outside surface of the inner wall.
Figure 8:
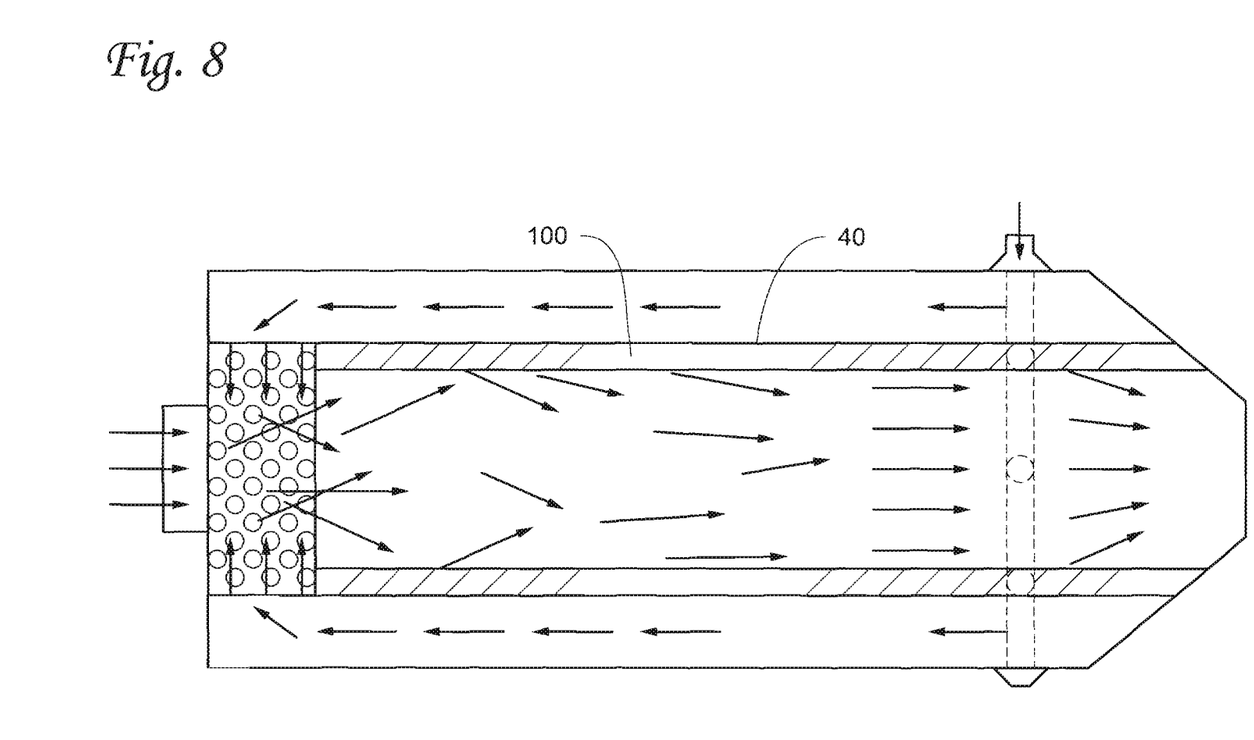
FIG. 8 is a view of an embodiment with an insulation layer on the inside surface of the inner wall.

In an alternative embodiment, the inner wall 40 can be provided with an insulation layer 100 that extends from the generally the second end of the wall 40 to generally the perforation pattern 50 to reduce heat transfer from the sample gas to the dilution gas, lowering the effect of thermophoresis by keeping the inner part of the wall the same temperature as the sample gas flowing through it. FIG. 7 illustrates an example of the insulation layer 100, for example a coated thin insulation material or a sealed chamber filled with insulation, connected to the outer surface of the wall 40. FIG. 8 illustrates a similar example, but with the insulation layer 100 connected to the inner surface of the wall 40.

Figure 2:
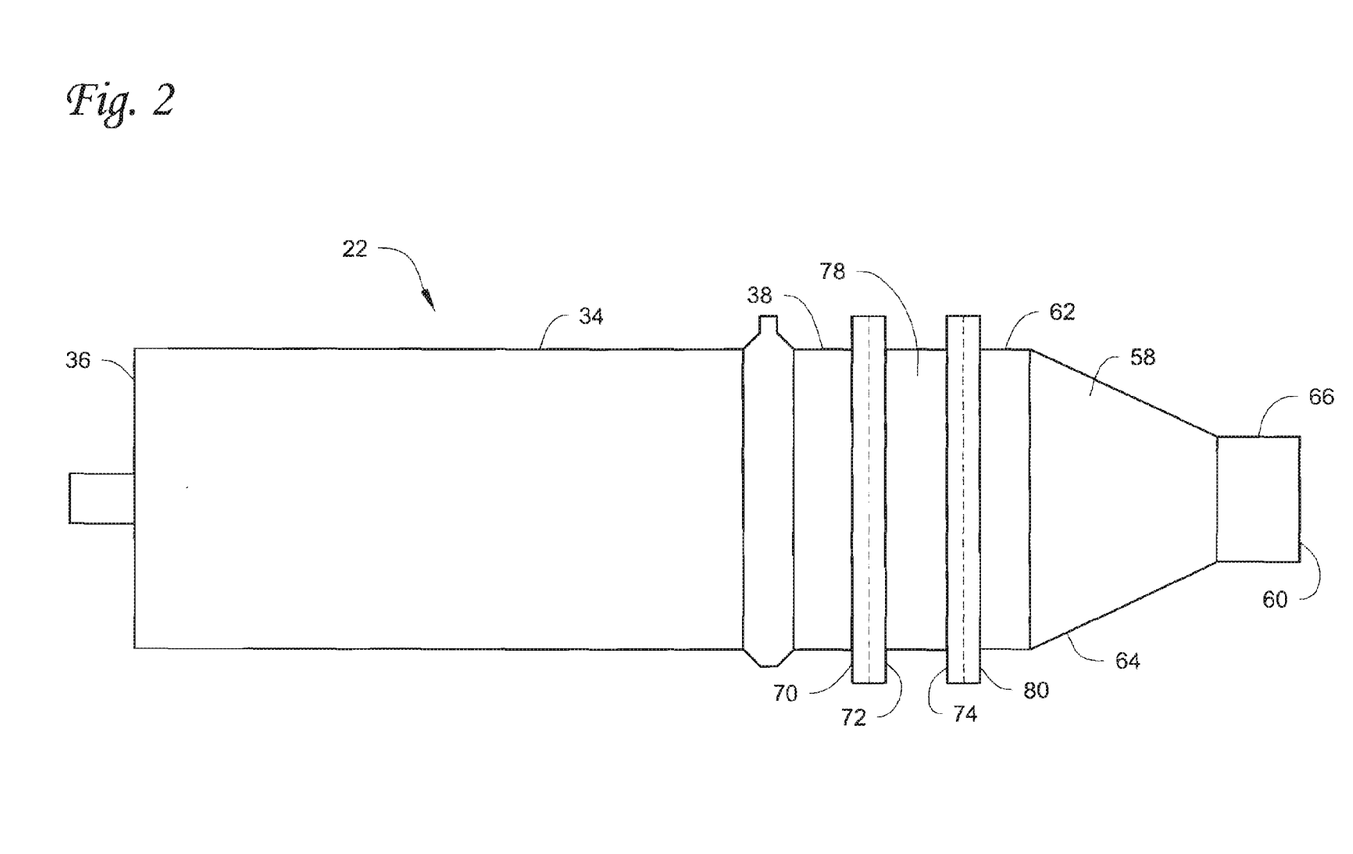
FIG. 2 is a side view of the dilution apparatus.

As shown in FIGS. 2-4, a reducing cone 58 is connected to the end of the housing 34 and defines an exit 60 for the mixture of sampled gas and dilution gas from the dilution apparatus 22. The reducing cone 58 includes a first constant diameter section 62 that connects to the housing 34, a tapered section 64 that reduces in diameter to reduce the diameter of the flow path, and a second constant diameter section 66 that defines the exit 60 and which is directly connected to the residence time chamber 24. The reducing cone 58 helps to provide a smooth flow transition of the gas mixture from the dilution apparatus 22 to the residence time chamber 24.

Preferably, the wall 40 is removably disposed within the housing 34. This permits removal of the wall 40 and replacement with a new wall having a different arrangement of perforations and/or a different length or diameter. As a result, replacement of the wall 40 permits adjustment in the perforations, and adjustments in the dimensions of the static pressure chamber 46 and the mixing chamber 48.

Figure 6:
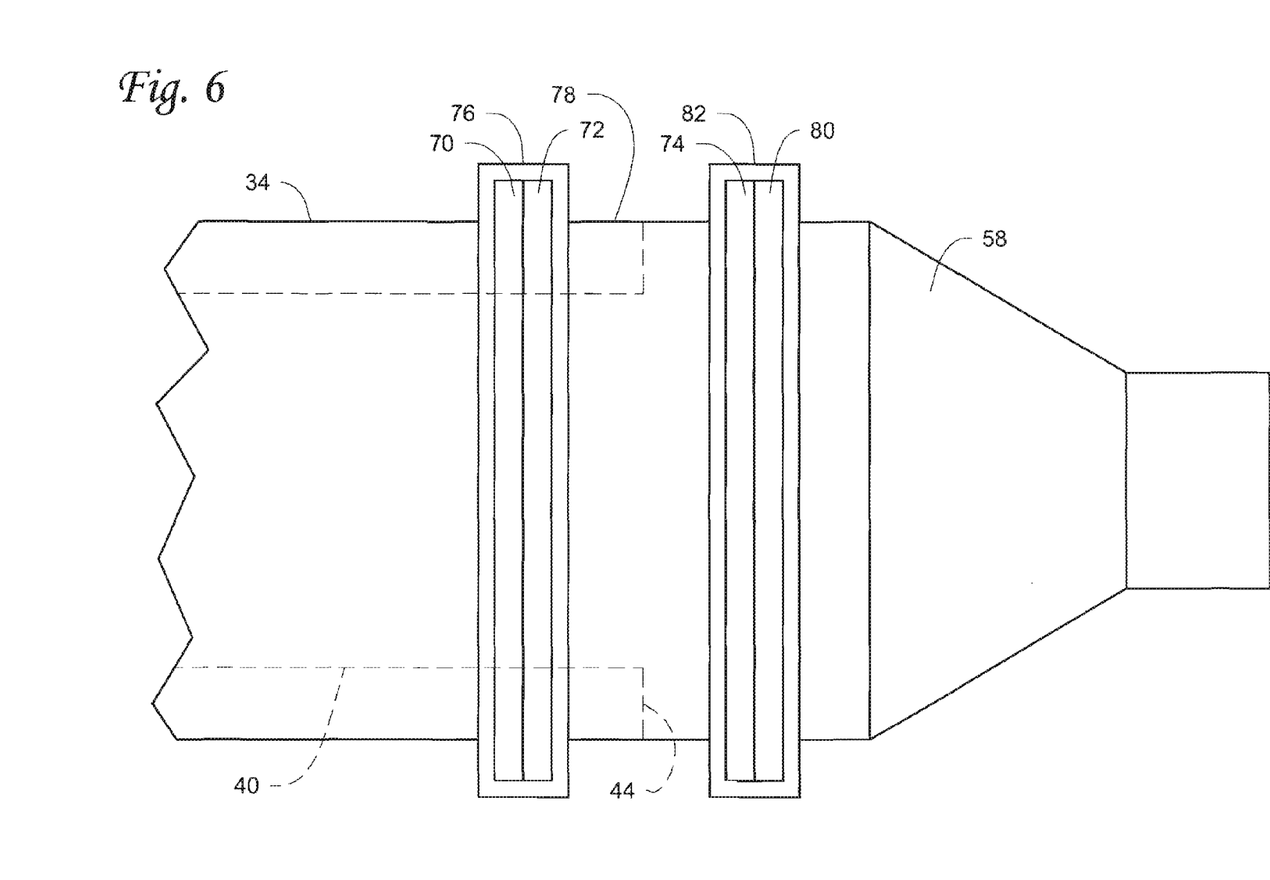
FIG. 6 is a partial sectional view of the dilution apparatus showing details in the area if the dilution gas inlet.

FIGS. 2, 3, 4 and 6 illustrate an example of how the wall 40 can be removably disposed within the housing 34. The second end 38 of the housing 34 is open and is provided with a radial flange 70. The wall 40 is a separate tube that is secured to a housing section 78 that includes a flange 72 at one end and a flange 74 at its opposite end. The constant diameter section 62 of the reducing cone 58 includes a flange 80 that is abutted against the flange 74. The wall 40 is inserted into the open end 38 of the housing 34 until the end 42 of the wall 40 abuts against and generally seals with the end 36 of the housing 34 (best seen in FIG. 5). At this position, the radial flange 72 formed on the housing section 78 abuts against the flange 70. The housing 34, wall 40, housing section 78, and reducing cone 58 are then secured together by suitable connectors 76 and 82 that engage the flanges 70 and 72, and 74 and 80, for example a band clamp (the connectors, which are shown in FIG. 6, are removed from FIGS. 2-4 for clarity). By disengaging the connectors 76 and 82, the housing 34, housing section 78, and reducing cone 58 can be disengaged, allowing removal of the wall 40 and replacement with a new wall and/or a new housing 34 if necessary.

The dilution apparatus 22 is preferably made of inert materials, including, but not limited to, stainless steel, plastic or polymer materials such as TEFLON, and plastic or polymer coated aluminum such as TEFLON-coated aluminum. In addition, the use of electrically non-chargeable materials, such as 304, 316 and 316L stainless steels, can also be used to reduce electrostatic deposition of charged particles that are typically polarized during combustion processes. In addition, the dilution apparatus 22 is preferably devoid of materials, for example oils, greases, rubbers and the like, that could outgas organics to avoid contamination of the gas stream flowing therethrough.

The operation of the dilution apparatus 22 is apparent from the preceding description. Sampled gas flowing through the mixing chamber 48 exchanges heat with the dilution gas, which is at a lower temperature than the gas in the mixing chamber, in the static pressure chamber 46. As apparent from the flow arrows in FIG. 4, the direction of flow of the dilution gas in the static pressure chamber is opposite the direction of flow of the gas in the mixing chamber. The dilution gas is then evenly introduced radially into the gas stream in the mixing chamber through the holes 50. The radial introduction produces turbulent mixing of the dilution gas and the sampled gas. In addition, because the dilution gas is introduced near the inlet end of the dilution apparatus 22, the sampled gas and mixing gas have a relatively long time to mix within the mixing chamber as the gases flow through the dilution apparatus toward the exit 60 and on to the residence time chamber.

The invention may be embodied in other forms without departing from the spirit or novel characteristics thereof. The embodiments disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A thermophoresis-resistant gas dilution apparatus, comprising:
   a housing having a first end and a second end and defining an interior space, the second end including an exit port in communication with the interior space through which gas exits the apparatus;
   a wall disposed within the interior space of the housing and dividing the interior space into an inner flow path defined by the wall and an outer flow path defined between the housing and the wall, the inner flow path being in communication with the exit port;
   a gas stream inlet adjacent the first end of the housing, the gas stream inlet opening into the inner flow path to permit introduction of a gas stream into the inner flow path;
   a dilution gas inlet in the housing adjacent the second end thereof, the dilution gas inlet opening into the outer flow path to permit introduction of dilution gas into the outer flow path, the dilution gas inlet comprises a plurality of inlet ports that are radial relative to a longitudinal axis of the housing; and
   a plurality of holes in the wall axially spaced from the dilution gas inlet that place the outer flow path in communication with the inner flow path;
   the apparatus is configured and arranged so that dilution gas introduced into the outer flow path is in heat exchange relationship with gas in the inner flow path over a substantial distance between the first end and the second end prior to the dilution gas in the outer flow path being introduced into the inner flow path.

2. The thermophoresis-resistant gas dilution apparatus of claim 1, wherein the housing and the wall are cylindrical.

3. The thermophoresis-resistant gas dilution apparatus of claim 1, wherein the inner flow path includes an inlet end adjacent the first end of the housing and an outlet end adjacent the second end of the housing; and the outer flow path includes an inlet end adjacent the dilution gas inlet, and an outlet end adjacent the first end of the housing; and the inlet end of the outer flow path is not in direct flow communication with the outlet end of the inner flow path.

4. The thermophoresis-resistant gas dilution apparatus of claim 1 wherein the gas stream inlet is coaxial to the longitudinal axis.

5. The thermophoresis-resistant gas dilution apparatus of claim 1 wherein the inlet ports are equally spaced circumferentially about the housing.

6. The thermophoresis-resistant gas dilution apparatus of claim 1, wherein the plurality of holes comprises a perforation pattern formed in the wall, the perforation pattern providing 20% to 80% (by area) porosity, and the holes are 0.125 inches to 0.5 inches in diameter.

7. The thermophoresis-resistant gas dilution apparatus of claim 1, wherein the housing has a length ranging from 18 inches to 63 inches, the housing has a diameter ranging from 3 inches to 10.5 inches, and a gap between the wall and the housing that forms the outer flow path ranges from 0.2 inches to 2.0 inches.

8. The thermophoresis-resistant gas dilution apparatus of claim 1, further comprising a reducing cone connected to the second end of the housing, the reducing cone defining the exit port.

9. The thermophoresis-resistant gas dilution apparatus of claim 1, wherein the wall is removably disposed within the housing.

10. The thermophoresis-resistant gas dilution apparatus of claim 1, further comprising an insulation layer located on the wall.

11. The thermophoresis-resistant gas dilution apparatus of claim 1, further comprising one or more of means for controlling the dilution ratio, means for conditioning the dilution gas, and means for heating or cooling the dilution gas.

12. A gas stream dilution apparatus for a source dilution sampling system comprising:
    a cylindrical housing having a first end, a second end and an interior space;
    an inner cylindrical wall located concentrically with said housing; the cylindrical wall having a first end adjacent the first end of the housing and a second end adjacent the second end of the housing; and the cylindrical wall dividing the interior space into a static pressure chamber defined between the housing and the wall and that extends generally from the first end of the wall to the second end of the wall, and a mixing chamber that extends generally from the first end of the wall to the second end of the wall;
    the wall having circumferentially and axially distributed perforations that place the static pressure chamber in communication with the mixing chamber, with the number of perforations being greater near the first end of the wall than near the second end of the wall;
    the housing having a plurality of inlet ports near the second end thereof that open into the static pressure chamber for introducing a dilution gas into the static pressure chamber, the inlet ports are radial relative to a longitudinal axis of the housing; and
    an inlet port adjacent the first end of the housing that opens into the mixing chamber for introducing a gas stream into the mixing chamber; the perforations in the wall allowing for the distribution into and mixing of dilution gas with a gas stream in the mixing chamber.

13. The gas stream dilution apparatus of claim 12, wherein the inlet port into the mixing chamber is coaxial to the longitudinal axis.

14. The gas stream dilution apparatus of claim 12, wherein the inlet ports of the housing are equally spaced circumferentially about the housing.

15. The gas stream dilution apparatus of claim 12, wherein the perforations provide 20% to 80% (by area) porosity, and the perforation are holes that are 0.125 inches to 0.5 inches in diameter.

16. The gas stream dilution apparatus of claim 12, wherein the housing has a length ranging from 18 inches to 63 inches, the housing has a diameter ranging from 3 inches to 10.5 inches, and a gap between the wall and the housing that forms the static pressure chamber ranges from 0.2 inches to 2.0 inches.

17. The gas stream dilution apparatus of claim 12, further comprising a reducing cone connected to the second end of the housing, the reducing cone defining an exit port of the apparatus.

18. The gas stream dilution apparatus of claim 12, further comprising an insulation layer located on the inner wall.

19. The gas stream dilution apparatus of claim 12, further comprising one or more of means for controlling the dilution ratio, means for conditioning the dilution gas, and means for heating or cooling the dilution gas.

20. A method of simulating atmospheric dilution, mixing and cooling of a gas stream, comprising:
    introducing a gas stream at a first temperature into a first chamber in which the gas stream can flow from a first end to a second end;
    introducing a dilution gas at a second temperature lower than the first temperature into a second chamber surrounding the first chamber and separated from the first chamber by a wall, the dilution gas being introduced into the second chamber through a plurality of inlet ports that are radial relative to a longitudinal axis of the first chamber, the second chamber having a heat exchange relationship with the first chamber so that the dilution gas in the second chamber exchanges heat with the gas stream in the first chamber, and with the dilution gas flowing through the second chamber in a direction opposite the direction of flow of the gas stream; and
    after a period of heat exchange between the dilution gas and the gas stream, evenly introducing the dilution gas into the gas stream through a plurality of holes in the wall located only near the first end of the first chamber.

21. The method of claim 20, wherein the gas stream comprises exhaust gas from an internal combustion engine.

22. The method of claim 20, comprising introducing the dilution gas into the gas stream in a radial direction relative to the direction of the gas stream flow.

23. The method of claim 20, comprising at least one of changing the dilution ratio, conditioning the dilution gas, and heating or cooling the dilution gas.

24. The thermophoresis-resistant gas dilution apparatus of claim 1, wherein the first wall has a first end adjacent the first end of the housing and a second end adjacent the second end of the housing, and the plurality of holes in the wall for placing the outer flow path in communication with the inner flow path are only near the first end of the wall.

* * * * *